United States Patent [19]
Roulier et al.

[11] Patent Number: 5,874,092
[45] Date of Patent: Feb. 23, 1999

[54] COMPOSITION IN THE FORM OF A SMOOTH PASTE AND PROCESS FOR ITS PREPARATION

[75] Inventors: Véronique Roulier, Paris; Dolorés Miguel-Colombel, L'Hay-Les Roses, both of France

[73] Assignee: L'Oreal, Paris, France

[21] Appl. No.: 685,685

[22] Filed: Jul. 24, 1996

[30] Foreign Application Priority Data

Jul. 25, 1995 [FR] France .................................. 95 09025

[51] Int. Cl.$^6$ .................................................. A61K 7/00
[52] U.S. Cl. ........................... 424/401; 424/64; 424/70.1; 424/70.7
[58] Field of Search ................. 528/324; 252/315.01; 424/195.1, 64, DIG. 5, 70.7, 70.1, 484, 401; 574/944, 783

[56] References Cited

U.S. PATENT DOCUMENTS

| | | |
|---|---|---|
| 3,911,105 | 10/1975 | Papantoniou et al. . |
| 3,937,811 | 2/1976 | Papantoniou et al. . |
| 5,066,486 | 11/1991 | Kamen et al. . |
| 5,437,859 | 8/1995 | Ser et al. . |
| 5,580,546 | 12/1996 | Ser et al. . |
| 5,674,508 | 10/1997 | Deserable et al. . |
| 5,679,361 | 10/1997 | Pradier et al. . |

FOREIGN PATENT DOCUMENTS

| | | |
|---|---|---|
| 0 602 905 | 12/1993 | European Pat. Off. . |
| 0 605 284 | 12/1993 | European Pat. Off. . |

*Primary Examiner*—Robert J. Hill, Jr.
*Attorney, Agent, or Firm*—Finnegan, Henderson, Farabow, Garrett & Dunner, L.L.P.

[57] ABSTRACT

A composition in smooth paste form which is particularly homogeneous although it comprises, on the one hand, at least one lipophilic component such as fatty substances and, on the other hand, at least one hydrophilic component such as polyhydric alcohols and/or an aqueous phase, and the process for preparing such a composition.

29 Claims, No Drawings

COMPOSITION IN THE FORM OF A SMOOTH PASTE AND PROCESS FOR ITS PREPARATION

The present invention relates to a composition, in particular a cosmetic of dermatological composition, in the form of a smooth paste which may be used to care for and/or to make up the lips and/or the skin. The invention also relates to a process for the preparation of this composition.

Cosmetic compositions which may be applied to the skin or the lips as a make-up or care product, such as bases for the lips or lipsticks, for example, may be, in a known manner, in the form of a solid stick, for example a lipstick pencil, or in the form of a smooth paste, which can be applied with a brush, for example.

Compositions in stick form generally comprise a large amount of waxes, as well as oils, pigments and/or fillers and, optionally, additives. Compositions in smooth paste form generally contain few or no waxes, which allows them to be taken up and applied easily, given that a large amount of waxes would lead to a composition of high viscosity, and thus one which is difficult to apply.

However, waxes make it possible to impart certain advantageous properties to the compositions comprising them, in particular qualities of creaminess of the composition and qualities of hold and of thickness of the film applied. Thus, it would be desirable to have available compositions in smooth paste form which may comprise large amounts of waxes.

Moreover, it would be advantageous to accentuate some of the cosmetic qualities of compositions in smooth paste form; in particular, it would be desirable to enhance further their softness when they are applied to the lips or the skin, while at the same time imparting a certain level of moisturization and care to the support.

Thus, it would be desirable to be able to incorporate, into compositions in smooth paste form, moisturizing or care ingredients such as, for example, polyhydric alcohols or active agents, in particular in dispersion or in solution in an aqueous phase. Now, it has been observed that polyhydric alcohols, and in particular glycerol, just like the gelled aqueous phases, are generally incompatible with fatty substances. The reason for this is that it has also been observed that a composition comprising fatty substances and glycerol is not in the form of a single homogeneous phase, but in the form of two separate phases, thereby introducing problems of conservation over time.

One of the solutions to overcome this drawback is to incorporate into the composition, in particular when it is in the form of a stick, a surfactant which makes it possible to maintain the composition in the form of a single homogeneous phase. However, the composition obtained may have a certain irritant nature.

It is also possible to choose the fatty substances as a function of the polyhydric alcohol, given that certain specific fatty substances are compatible with certain polyhydric alcohols, for example isoprene-glycol; however, this introduces a great limitation as regards the formulations which may be envisaged.

The aim of the present invention is to overcome these drawbacks, and the invention proposes a composition in smooth paste form which is particularly homogeneous, although it comprises, on the one hand, lipophilic components such as fatty substances and, on the other hand, hydrophilic components such as polyhydric alcohols and/or an aqueous phase.

One subject of the present invention is thus an extruded composition in the form of a smooth paste, comprising a lipophilic component and a hydrophilic component, the said composition being in the form of a single homogeneous phase.

Another subject of the invention is a process for the preparation of the said composition, in which at least part of the process is carried out using a mixer-extruder.

Thus, generally, the process according to the invention makes it possible to obtain a homogeneous composition from two mutually incompatible phases, one of these phases being lipophilic and the other being hydrophilic.

An advantage of the invention is that it allows the preparation of homogeneous compositions of varied formulation, without being restricted by the presence of a certain type of fatty substance.

Moreover, the composition obtained may be stable and homogeneous even if it contains no or essentially no surfactants. As defined herein, the phrase "essentially no surfactants" means an amount of surfactant insufficient to maintain the composition in the form of a single homogeneous phase when one skilled in the art tries to obtain a single homogeneous phase solely by using a surfactant.

The composition according to the present invention is thus a smooth paste the viscosity of which may be measured, in contrast with the solid structure of a pencil or stick, the viscosity of which cannot be measured. The said dynamic viscosity at 25° C. generally ranges from 3 to 35 Pa s, measured with a Contraves TV rotary viscometer equipped with an "MS-r4" rotor at a frequency of 60 Hz.

The composition according to the invention thus comprises at least one lipophilic component, which may be chosen, for example, from the usual constituents of a fatty phase such as waxes, oils, gums and/or fatty substances which are pasty, hydrocarbon-containing and/or silicone-containing, and possibly volatile, alone or as a mixture.

Among the waxes which may be envisaged, alone or as a mixture, mention may be made of mineral waxes such as microcrystalline waxes, paraffin, petrolatum, petroleum jelly, ozokerite and montan wax; animal waxes such as beeswax, lanolin and derivatives thereof; plant waxes such as candelilla wax, ouricurry wax, carnauba wax, Japan wax, cocoa butter, cork fibre wax or sugar cane wax; hydrogenated oils, fatty esters and glycerides which are solid at 25° C.; synthetic waxes such as polyethylene waxes and the waxes obtained by Fischer-Tropsch synthesis; silicone waxes; mixtures thereof.

Among the oils which may be envisaged, alone or as a mixture, mention may be made of mineral oils such as paraffin oil or liquid petroleum jelly; animal oils such as perhydrosqualene or arara oil; plant oils such as sweet almond oil, calophyllum oil, palm oil, castor oil, avocado oil, jojoba oil, olive oil or cereal germ oil; silicone oils such as polydimethyl-siloxane; esters of lanolic acid, of oleic acid, of lauric acid, of stearic acid or of myristic acid, for example; alcohols such as oleyl alcohol, linoleyl alcohol, linolenyl alcohol, isostearyl alcohol or octyldodecanol; alcohol or polyalcohol acetylgly-cerides, octanoates, decanoates or ricinoleates; volatile oils such as cyclotetradimethylsiloxane, cyclopentadimethylsiloxane, cyclohexadimethylsiloxane and methylhexyldimethylsiloxane, or isoparaffins.

The composition may preferably comprise from 65 to 99% by weight of lipophilic component, which may preferably contain from 8 to 40% by weight of waxes and from 60 to 92% by weight of oils.

By means of the process used to prepare the present composition, it is possible to add a large amount of waxes into the composition, for example at least 10% and more preferably about 15–25% by weight, without incurring any problem of homogeneity or of formation of grains. Thus, the composition obtained having a high wax content is capable of forming a film which is of good hold.

The composition according to the invention also comprises at least one hydrophilic component, which may be a polyhydric alcohol and/or which may be in the form of a gelled aqueous phase.

The polyhydric alcohol may preferably be a compound having 2–8 carbon atoms and 2–6 hydroxyl functions, such as ethylene glycol, isoprene-glycol, glycerol, 1,2-propanediol, diglycerol, erythritol, arabitol, adonitol, sorbitol and dulcitol. The polyhydric alcohol may also be a polyether alcohol with a weight average molecular weight of 150–600, such as polyethylene glycol 300 and polyglycerol 500. A mixture of polyhydric alcohols may also be used.

The gelled aqueous phase may be gelled by the presence of any gelling agent known to those skilled in the art.

As a gelling agent, mention may be made in particular of:

alga extracts such as agar-agar, carrageenans and alginates, seed extracts such as extracts of carob or of guar, fruit extracts, in particular pectin, plant exudates, such as gum arabic, gum tragacanth, karaya gum and ghatti gum, cellulose derivatives such as carboxymethyl cellulose, gelling agents of animal origin such as gelatin or caseinates, exudates of microorganisms such as xanthan gum, synthetic gelling agents such as acrylic polymer derivatives (Carbomer, Carbopol, Pemulen) or silicates (compounds based on silicon such as Laponite, Lapomer or Veegum).

The gelling agent may preferably be present in the aqueous phase in a proportion of 0.2–10% by weight relative to the aqueous phase.

The hydrophilic component may have a viscosity preferably ranging from 1 to 250 poises, more preferably 30 to 250 poises. As regards the lipophilic component, this may have a viscosity higher or lower than that of the hydrophilic component.

The composition may preferably comprise 1–35% by weight of hydrophilic component, more preferably 3–15% by weight, the hydrophilic component possibly also being in the form of a mixture of gelled aqueous phase and of polyhydric alcohol.

The composition may also comprise any constituent usually used in the field of application envisaged, and in particular antioxidants, fragrances, essential oils, preserving agents, cosmetic active agents, moisturizing agents, vitamins, essential fatty acids, sphingolipids, sunscreens, surfactants, dyes, pigments, pearlescent agents, fillers and polymers.

Depending on the nature of these additional constituents, they will be added to the lipophilic component or to the hydrophilic component during the preparation of the composition. A person skilled in the art will know how to select these possible additional constituents, as well as their amount, such that the advantageous properties of the composition according to the invention are not, or are substantially not, altered by the addition envisaged.

The composition according to the invention may be in the form of a make-up product for the skin, in particular in the form of a foundation, a blusher, an eyeshadow, a mascara, an eyeliner, a lip composition or a base for the lips, or alternatively in the form of a care product for the skin or an antisun or self-tanning product, or even in the form of a hair product.

The composition according to the invention makes it possible to obtain a film which spreads easily and uniformly, and which has a certain softness. The film obtained has a light texture and remains comfortable to wear throughout the day. It is also of good hold. The composition obtained also has good emollient properties when applied to the skin.

The composition according to the invention may advantageously be prepared using a mixer-extruder. A mixer-extruder is generally composed of several parts that can be heated at different temperatures.

It is possible, for example, to prepare a premix comprising at least some of the various constituents of the composition, including at least a portion of those having a high melting point, to heat this premix to a temperature at which it melts, and then to add the rest of the constituents, in one or more portions, and to blend the mixture obtained in a mixer-extruder, during at least part of its period of cooling to room temperature.

For example, it is possible to add all the components with a high melting point in a first part A, and then to add, in a part B or in different parts B, C, D, etc., the remaining components. It is also possible, for example, to add in a first part A, some of the high melting point components, then in a part B, or in parts B, C, D, etc., the other high melting point components, and then to add in one or several parts, J, K, L, etc., the remaining components.

It is also possible to introduce all of the constituents into the top of the mixer-extruder, under hot or cold conditions, then optionally to increase the temperature of the said mixture so as to obtain a homogeneous mixture, while at the same time blending, and to continue the blending for at least part of the period of cooling to room temperature.

It has, indeed, been observed that this process makes it possible to obtain a composition in the form of a smooth and homogeneous paste, although it contains a hydrophilic component and a lipophilic component.

The heating step may be carried out according to any known technique and, in particular, directly in the extruder.

The various steps of the process may be performed in one or more extruders arranged one after the other, and preferably in a single twin-screw extruder.

It has, indeed, been observed that the composition obtained after extrusion is particularly soft and affords a certain silky sensation when it is applied to the skin, while at the same time avoiding the appearance and sensation of an oily grease.

The conditions under which the extrusion may be carried out are described in patent application FR94/00756, the disclosure of which is specifically incorporated into the present application by way of reference.

The invention is illustrated in greater detail in the concrete examples which follow, without any limitation being implied.

EXAMPLE 1

A lip composition in smooth paste form and having the following composition was prepared:

| | |
|---|---|
| jojoba oil | 15 g |
| castor oil | 10 g |
| lanolin | 10 g |
| beeswax | 10 g |
| polyethylene wax | 15 g |
| polybutene | 5 g |
| polyglycerol | 20 g |
| pigments and fillers | 15 g |

The hydrophilic and lipophilic phases were introduced separately into a twin-screw extruder, at an inlet temperature of about 85°–95° C. and an outlet temperature of 30° C. The screw speed was set at about 400 revolutions/minute.

A smooth paste of viscosity equal to 13 Pa s was obtained at the outlet, in the form of a single, stable and homogeneous phase, and which could be taken up for application using a brush. This composition made it possible to obtain a homogeneous film which spread easily and was very soft. The film obtained also had a light texture and was comfortable to wear throughout the day.

EXAMPLE 2

A lip composition in smooth paste form and having the following composition was prepared:

| | |
|---|---|
| jojoba oil | 20 g |
| liquid petroleum jelly | 20 g |
| lanolin | 20 g |
| candelilla wax | 7 g |
| polyethylene wax | 10 g |
| isoprene-glycol | 1 g |
| pigments | 12 g |
| fillers (talc and nylon powder) | 10 g |

The composition was prepared according to Example 1. A homogeneous composition which has good cosmetic properties was obtained.

EXAMPLE 3

A treating base for the lips, in smooth paste form and having the following composition, was prepared according to Example 1:

| | |
|---|---|
| liquid petroleum jelly | 22 g |
| isopropyl lanolate | 20 g |
| lanolin | 20 g |
| microcrystalline wax | 15 g |
| carnauba wax | 10 g |
| glycerol | 10 g |
| tocopheryl acetate | 2 g |
| octyl methoxycinnamate | 1 g |

The composition was in the form of a single homogeneous phase and had good cosmetic properties, a certain level of softness on application and good moisturizing properties.

EXAMPLE 4

A composition was prepared according to Example 1, comprising:

| | |
|---|---|
| liquid petroleum jelly | 22 g |
| isopropyl lanolate | 20 g |
| lanolin | 20 g |
| microcrystalline wax | 15 g |
| carnauba wax | 10 g |
| gelled aqueous phase (0.1 g of Carbopol + 9.9 g of water) | 10 g |
| tocopheryl acetate | 2 g |
| octyl methoxycinnamate | 1 g |

A composition in the form of a single, stable and homogeneous phase was obtained. It allowed a homogeneous film which spreads easily to be obtained.

EXAMPLE 5

A composition was prepared according to Example 1, comprising:

| | |
|---|---|
| liquid petroleum jelly | 17 g |
| isopropyl lanolate | 15 g |
| lanolin | 15 g |
| microcrystalline wax | 15 g |
| carnauba wax | 10 g |
| tocopheryl acetate | 2 g |
| octyl methoxycinnamate | 1 g |
| gelled aqueous phase (1.25 g carboxymethyl cellulose + 23.75 g of water) | 25 g |

A composition in the form of a single, stable and homogeneous phase which has good cosmetic properties was obtained.

EXAMPLE 6

Comparative Example

A lip composition in standard smooth paste form and having the following composition was prepared:

| | |
|---|---|
| liquid petroleum jelly | 62 g |
| isopropyl lanolinate | 10 g |
| lanolin | 10 g |
| microcrystalline wax | 2 g |
| glycerol | 5 g |
| pigments | 5 g |

The various ingredients were mixed together at 100° C. using a Moritz-type stirrer. A heterogeneous mixture which was in two phases was obtained. It was not possible to obtain a homogeneous dispersion with this process. If the wax content was increased, for example to 8%, it was still not possible to obtain a homogeneous mixture.

We claim:

1. A smooth paste comprising at least one lipophilic component and at least one hydrophilic component, wherein said smooth paste comprises no surfactant or essentially no surfactant and is in the form of a single homogeneous phase having a dynamic viscosity at 25° C. ranging from 3 to 35 Pa s, measured with a Contraves TV rotary viscometer equipped with an MS-r4 rotor at a frequency of 60 Hz.

2. A smooth paste according to claim 1, wherein said at least one hydrophilic component is a polyhydric alcohol, is in the form of a gelled aqueous phase, or is a polyhydric alcohol in the form of a gelled aqueous phase.

3. A smooth paste according to claim 2, wherein said at least one hydrophilic component is a polyhydric alcohol having 2–8 carbon atoms and 2–6 hydroxyl functions.

4. A smooth paste according to claim 2, wherein said at least one hydrophilic component is ethylene glycol, isoprene-glycol, glycerol, 1,2-propanediol, diglycerol, erythritol, arabitol, adonitol, sorbitol, dulcitol, or a polyether alcohol with a weight average molecular weight of 150–600.

5. A smooth paste according to claim 4, wherein said at least one hydrophilic component is a polyether alcohol, and wherein said polyether alcohol is polyethylene glycol 300, polyglycerol 500 or a mixture thereof.

6. A smooth paste according to claim 2, wherein said at least one hydrophilic component is in the form of a gelled aqueous phase or is a polyhydric alcohol in the form of a gelled aqueous phase, wherein at least one gelling agent is used to gel said gelled aqueous phase, and further wherein said at least one gelling agent is selected from the group consisting of:

alga extracts;
seed extracts;

fruit extracts;

plant exudates;

cellulose compounds;

gelling agents of animal origin;

exudates of microorganisms; and synthetic gelling agents.

7. A smooth paste according to claim 6, wherein said at least one gelling agent is selected from the group consisting of agar-agar, carrageenans, alginates, carob extract, guar extract, guar extract, pectin, gum arabic, gum tragacanth, karaya gum, ghatti gum, carboxymethyl cellulose, gelatin, caseinates xanthan gum, acrylic polymers and silicates.

8. A smooth paste according to claim 7, wherein said at least one gelling agent is present in the aqueous phase in a proportion of 0.2–10% by weight, relative to the aqueous phase.

9. A smooth paste according to claim 1, wherein said smooth paste is an extruded smooth paste.

10. A smooth paste according to claim 1, wherein said at least one hydrophilic component has a viscosity ranging from 1 to 250 poises.

11. A smooth paste according to claim 10, wherein said at least one hydrophilic component has a viscosity ranging from 30 to 250 poises.

12. A smooth paste according to claim 1, wherein said at least one lipophilic component is a wax, an oil, a gum, or a fatty substance, and wherein said at least one lipophilic component has at least one characteristic selected from the group consisting of pasty, hydrocarbon-containing, silicone-containing, and volatile.

13. A smooth paste according to claim 1, wherein said at least one hydrophilic component is present in an amount ranging from 1 to 35% by weight, relative to the total weight of the smooth paste.

14. A smooth paste according to claim 13, wherein said at least one hydrophilic component is present in an amount ranging from 3 to 15% by weight, relative to the total weight of the smooth paste.

15. A smooth paste according to claim 1, wherein said at least one lipophilic component is present in an amount ranging from 65 to 99% by weight, relative to the total weight of the smooth paste.

16. A smooth paste according to claim 15, wherein said at least one lipophilic component comprises at least one wax in an amount ranging from 8 to 40% by weight, relative to the total weight of said lipophilic component and at least one oil in an amount ranging from 60 to 92% by weight, relative to the total weight of said lipophilic component.

17. A smooth paste according to claim 1, wherein at least one wax is present in an amount of at least 10%, relative to said smooth paste.

18. A smooth paste according to claim 17, wherein said at least one wax is present in an amount ranging from 15 to 25%, relative to said smooth paste.

19. A smooth paste according to claim 1, wherein said smooth paste comprises no surfactant.

20. A smooth paste according to claim 1, wherein said smooth paste comprises essentially no surfactant.

21. A smooth paste according to claim 1, wherein said smooth paste is in the form of a make-up product, a care product for the skin, an antisun or self-tanning product, or a hair product.

22. A smooth paste according to claim 21, wherein said smooth paste is in the form of a make-up product, and wherein said make-up product is a foundation, a blusher, an eyeshadow, a mascara, an eyeliner, a lip composition or a base for the lips.

23. A process for the preparation of a smooth paste according to claim 1, comprising the step of combining at least one lipophilic component and at least one hydrophilic component, wherein at least part of said step of combining is carried out using a mixer-extruder, said step of combining further being carried out under conditions sufficient to form said smooth paste in the form of a single homogeneous phase.

24. A process according to claim 23, wherein said step of combining comprises the steps of:

(a) preparing a premix comprising at least some of said at least one lipophilic component and at least one hydrophilic component including those of said at least one lipophilic component and said at least one hydrophilic component having a high melting point;

(b) heating said premix to a temperature at which it melts;

(c) adding the rest of said at least one lipophilic component and said at least one hydrophilic component in one or more portions to form a mixture; and (d) then cooling said mixture to room temperature, at least part of the time during which said mixture is blended in a mixer-extruder.

25. A process according to claim 23 comprising the steps of:

(a) introducing all of said at least one lipophilic component and said at least one hydrophilic component into the top of said mixer-extruder, under hot or cold conditions to form a mixture;

(b) optionally increasing the temperature of said mixture to obtain a homogeneous mixture, while at the same time blending; and (c) cooling, if appropriate, said mixture to room temperature while continuing the blending for at least part of the period of cooling.

26. A process according to claim 23, wherein said at least part of said step of combining carried out using a mixer-extruder is a heating step carried out in a mixer-extruder.

27. A process according to claim 23, wherein said at least part of said step of combining carried out using a mixer-extruder are various steps of the process performed in one or more mixer-extruders arranged one after the other.

28. A process according to claim 23, wherein said at least part of said step of combining carried out using a mixer-extruder are various steps of the process performed in a single twin-screw mixer-extruder.

29. An extruded smooth paste comprising at least one lipophilic component and at least one hydrophilic component, wherein said extruded smooth paste comprises essentially no surfactant and is in the form of a single homogeneous phase having a dynamic viscosity at 25° C. ranging from 3 to 35 Pa s, measured with a Contraves TV rotary viscometer equipped with an MS-r4 rotor at a frequency of 60 Hz.

* * * * *